(12) United States Patent
Dala-Krishna et al.

(10) Patent No.: US 7,211,045 B2
(45) Date of Patent: May 1, 2007

(54) METHOD AND SYSTEM FOR USING ULTRASOUND IN CARDIAC DIAGNOSIS AND THERAPY

(75) Inventors: Praveen Dala-Krishna, Bensalem, PA (US); Charles Bryan Byrd, Medford, NJ (US); David Jenkins, Flanders, NJ (US); Charles Lee Byrd, Weston, FL (US)

(73) Assignee: EP Medsystems, Inc., Mt. Arlington, NJ (US)

( * ) Notice: Subject to any disclaimer, the term of this patent is extended or adjusted under 35 U.S.C. 154(b) by 347 days.

(21) Appl. No.: 10/620,517

(22) Filed: Jul. 16, 2003

(65) Prior Publication Data

US 2004/0127798 A1 Jul. 1, 2004

Related U.S. Application Data

(60) Provisional application No. 60/397,653, filed on Jul. 22, 2002.

(51) Int. Cl.
*A61B 8/06* (2006.01)
(52) U.S. Cl. .................. 600/441; 600/450; 600/453
(58) Field of Classification Search ........ 600/407–472; 128/916; 601/2–3
See application file for complete search history.

(56) References Cited

U.S. PATENT DOCUMENTS 5,183,040 A * 2/1993 Nappholz et al. ............. 607/4
5,471,988 A 12/1995 Fujio et al.
5,749,833 A 5/1998 Hakki et al.
5,803,083 A 9/1998 Buck et al.
5,840,030 A 11/1998 Ferek-Petric et al.
6,120,453 A * 9/2000 Sharp .......................... 600/463

OTHER PUBLICATIONS

International Search Report for International Application No. PCT/US03/22351, dated Dec. 8, 2003.
Tortoli et al., Ultrasound Med. Biol., 28, 249-257 (2002).
Mohan et al., Pediat. Cardiol., 23, 58-61 (2002).
Pislaru et al., Journ. Amer. College Cardiol., 38, 1748-1756 (2001).
Krishna et al., Ultrasound Med. Bio., 23, 453-459 (1997).
Schrope et al., Ultrasound Med. Bio., 19, 567-579 (1993).
Krishna et al., Phys. Med. Biol., 44, 681-694 (1999).
Jan et al., Cardiovasc. Intervent. Radiol., 24, 84-89, (2001).
Tortoli et al., Ultrasound Med. Biol., 21, 527-532 (1995).

* cited by examiner

*Primary Examiner*—Ali Imam
(74) *Attorney, Agent, or Firm*—Fitch, Even, Tabin & Flannery (57) ABSTRACT

A method and system for estimating the volume of blood ejected from the left ventricle of the heart to a succeeding chamber/conduit, or vice-versa, while imaging the intersection of such structures is described. The process utilizes either the M-mode to estimate volume differences in a view of the ventricle over time or Doppler processing techniques to obtain flow profiles across intersections (e.g., valves), or blood vessels, which are then utilized to calculate output. This process can be combined with ECG guidance/triggering to measure/track changes in output from beat to beat, or during the course of an evaluation or therapeutic procedure. This process can be specifically used for the placement of permanent pacemaker electrodes.

35 Claims, 7 Drawing Sheets

METHOD AND SYSTEM FOR USING ULTRASOUND IN CARDIAC DIAGNOSIS AND THERAPY

RELATED APPLICATION

This application is based on, and claims benefit of, U.S. Provisional Application Ser. No. 60/397,653, filed on Jul. 22, 2002, which is herby incorporated by reference.

FIELD OF THE INVENTION

The present invention relates to a technique for measuring cardiac output (i.e., total volume of blood ejected by the left ventricle in one cardiac cycle). It is achieved either by measuring volumetric flow at the entrance of the aorta, or by measuring the change in volume of the left ventricle through a cardiac cycle, using ultrasonic imaging and pulse wave Doppler techniques.

BACKGROUND OF THE INVENTION

Volumetric output of blood from the heart and/or circulatory system are of interest in various diagnostic and therapeutic procedures. Such measurements are of significant interest during electrophysiological evaluation/therapy to first evaluate the extent of dysfunction due to arrhythmia and subsequently to judge the effect/effectiveness of any ablations/therapeutic procedures that are carried out on the cardiac muscle/conduction system. Iwa et al., *Eur. J. Cardithorac. Surg.*, 5, 191–197 (1991).

Ultrasound is the imaging modality of choice, especially in cardiology, since this modality offers real-time imaging capabilities of the moving heart. Further, advances through Doppler techniques allow the physician to visualize as well as measure blood flow. Pulse wave and continuous wave Doppler have proven to be quite accurate, and an effective way of evaluating flow through various parts of the circulatory system, especially the heart. Tortoli et al., *Ultrasound Med. Bio.*, 28, 249–257 (2002); Mohan et al., *Pediatr. Cardiol.* 23, 58–61 (2002); Ogawa et al., *J. Vasc. Surg.*, 35, 527–531 (2002); Pislaru et al., *J. Am. Coll. Cardiol.*, 38, 1748–1756 (2001).

Other technologies, including washout curves of contrast agents have been proposed to measure flow volume, especially to compensate for loss of signal quality due to imaging depth. Krishna et al., *Ultrasound Med. Bio.*, 23, 453–459 (1997); Schrope et al., *Ultrasound Med. Bio.*, 19, 567–579 (1993).

However, till recent advances in miniaturized ultrasonic transducers, physicians were limited to only certain angles of view, thus limiting the range and effectiveness of possible measurements. Further, given the depth of imaging required by such classical approaches, associated interrogation frequency limitations due to attenuation restricted the accuracy of measurement. Krishna et al., *Phys. Med. Biol.*, 44, 681–694 (1999). With the recent introduction of catheter based transducers for imaging the heart from either the vena-cava or even from within the heart, such limitations on frequency of interrogation and angle of view are not applicable.

One specific need for this invention is for the permanent placement of cardiac pacing electrodes. Cardiac pacing has been around for many years, and essentially involves the placement of a permanent electrode in the right ventricle to quicken the pace of an otherwise slow heart. A new therapy has recently been introduced to the market, Which involves pacing of the left ventricle in conjunction with the right ventricle in an effort to "resynchronize" the heart, that is, to coordinate the left ventricle's contraction in time with the contraction of the right ventricle. One problem in the current therapy is the optimization of the placement of the left ventricular electrode so as to provide maximum therapy. This invention addresses this problem by providing intracardiac ultrasound imaging and ultrasound Doppler as a new tool in the placement of the electrode.

SUMMARY OF THE INVENTION

Heart failure is a disease where the heart's main function, a pump for blood, is wearing down. The heart tissue can absorb fluid, the left ventricle does not allow quick electrical conduction, becomes enlarged, does not contract well, and becomes less efficient at pumping blood. A measurement for the efficiency of the heart as a pump is called "ejection fraction" or "EF. EF is measured as the percentage of blood contained in the ventricles that is pumped out with each beat of the heart. A healthy, young heart will have an EF greater than 90 (i.e., 90 percent of the ventricular blood is pumped with each heart beat); an older, sick heart in heart failure can have an EF less than 30. Heart failure leads to an extremely diminished lifestyle, and, left untreated, can be a major cause of mortality.

A new therapy to treat heart failure is bi-ventricular pacing, or "resynchronization" therapy, where both ventricles of the heart are paced with an implantable pulse generator, commonly known as an artificial pacemaker. Normal pacing for a slow heart is performed via an implanted electrode in the right ventricle. The conduction myofibers (Purkinje fibers) conduct the electrical pulse and the ventricles contract synchronously in an inward direction, resulting in blood being pumped efficiently from the heart. In heart failure, the left ventricle becomes enlarged and conduction through the tissue of the left ventricular wall often becomes slow, so that the upper part of the left ventricle conducts as much as 200 to 250 milliseconds behind the apex area of the ventricles. This leads to poor and discoordinated contraction, and in many cases, an outward movement of the heart muscle, so that blood sloshes around rather than being squeezed out of the ventricle. Thus, an ideal location to place a pacing electrode in the left ventricle is in the area of slowest conduction, which can be a rather large area of the left ventricle, and may not always be the area that has the largest conduction. The problem facing physicians today is to locate the optimal spot for the permanent fixation of the pacing electrode. The thrust of this invention is to provide a method and device to optimize the location of the electrode.

A normal pacemaker electrode is ideally implanted in a location which achieves the lowest "threshold," which is the lowest voltage level to excite the surrounding tissue to synchronously conduct the pacing signal from the electrode. Thus, the electrode is implanted based upon merely finding the spot with the lowest voltage that "captures" the tissue. With heart failure, in the left ventricle, it is not so simple. Capture may not be the best parameter to use. Furthermore, advancing the electrode to the proper spot may not be easy. What is most desired is to optimize EF, while the threshold for "capture" is really secondary. Thus the ability to not only visualize the motion of the left ventricular wall, but also measure EF, or some form of output of the heart, such as stroke volume or flow rate, is highly desirable during the implantation procedure. This invention puts forth the use of ultrasound technology for this purpose.

The present invention is directed to a method and system for measuring volumetric flow, specifically cardiac output, either with minimal intervention/input from the physician, or automatically, with the user of the system pre-specifying certain operating parameters/measurement criterion. One embodiment of the present invention is in the form of hardware and/or software that exists as part of the ultrasound scanner. In such an embodiment, the system utilizes the Doppler processing capabilities of the host ultrasound scanner to obtain a time-varying signal representative of the velocity of flow through an area of interest. Such area could include the inlet of the aorta from the left ventricle, or the valve in between. The system also utilizes a view/measure of the cross-sectional area through which the flow of interest is to pass.

The Doppler signals, the boundaries of which can be either demarcated by the user, or automatically estimated by the system, along with the measure of the cross-sectional area through which such flow passes, which can again be either demarcated/input by the user, or can be automatically measured by the system, are utilized by the processor, or any other hardware, software, or combination thereof, to calculate volume of flow through the area of interest.

Other embodiments also include the measuring system, either in the form of software and hardware or a combination thereof on a separate workstation/computer that is capable of obtaining relevant data from the examining ultrasound scanner either directly or indirectly, methods of being triggered/correlating the ultrasonic/Doppler signals (video/audio) with the electrocardiogram (ECG) of the subject being examined.

Another embodiment of the present invention utilizes the Doppler audio output of the Doppler processing system/subsystem in the ultrasound machine in addition to the facilities to obtain the measure of the area of interest through which the flow is to pass, and the ECG of the subject being examined. Again, this process/system can be embodied within the hardware and/or software of the ultrasound scanner, or implemented as a workstation and/or computer separate from the ultrasound scanner with facilities to communicate either directly or indirectly with the ultrasound scanner. Such processing then uses the frequency, phase and amplitude of the audio signals along with the measure of the area of interest through which the flow exists to calculate the volume of flow. A further embodiment can also include methods of obtaining ECG data from the subject being scanned to enhance the demarcation and/or separation of signals from beat to beat of the heart, or to assess either automatically, or aided by a user, the condition of the cardiac system and hence the factors effecting the acquired Doppler data.

The M-mode based embodiment would include hardware and/or software, either on the ultrasound system, or on a separate system that directly or indirectly communicates/receives data from the ultrasound system and a device that can digitize and/or transmit ECG data, if separate from the ultrasound unit. This device would then utilize these signals, in coordination with the ECG signals to calculate the spacing between the walls of the left ventricle to obtain the maximum and minimum volumes of the ventricle in the course of a cardiac cycle.

Ultrasound, as an imaging tool, has been around for some time. However, imaging through the chest is very difficult in that the ribs block the view and that the depth of penetration gives poor resolution. Ideally, the ultrasound transducer should be positioned closer to the heart. An esophageal ultrasound probe has been used on more than 50 patients in an attempt to view the heart. See, e.g., Jan et. al., *Cardiovasc. Intervent. Radiol.*, 24, 84–89 (2001). Unfortunately, the results are less than desired since the probe must view through the esophagus and both walls of the heart, lending to less resolution in the image than desired. Intravascular ultrasound systems, although ideal in its size with thin catheters, generally utilize with high frequencies which result in poor depth of penetration. X-ray or X-ray fluoroscopy may give good images of the electrode, but not of the actual tissue of the heart (most particularly the walls of the ventricle).

The present invention overcomes these problems. Preferably, the present invention uses an ultrasound imaging catheter designed for intracardiac use. Such an intracardiac catheter is generally sized as 10 French or less, has multiple elements on the transducer (e.g., 48 or 64 elements), employs lower frequencies (e.g., about 5 and about 10 MHz), and uses a phased array transducer for optimal resolution. Not only will this allow the imaging of wall motion for this specific purpose of a left ventricular electrode fixation, but will also, especially if used in conjunction with Doppler techniques, provide information to calculate measurement of cardiac output.

Figure 6:
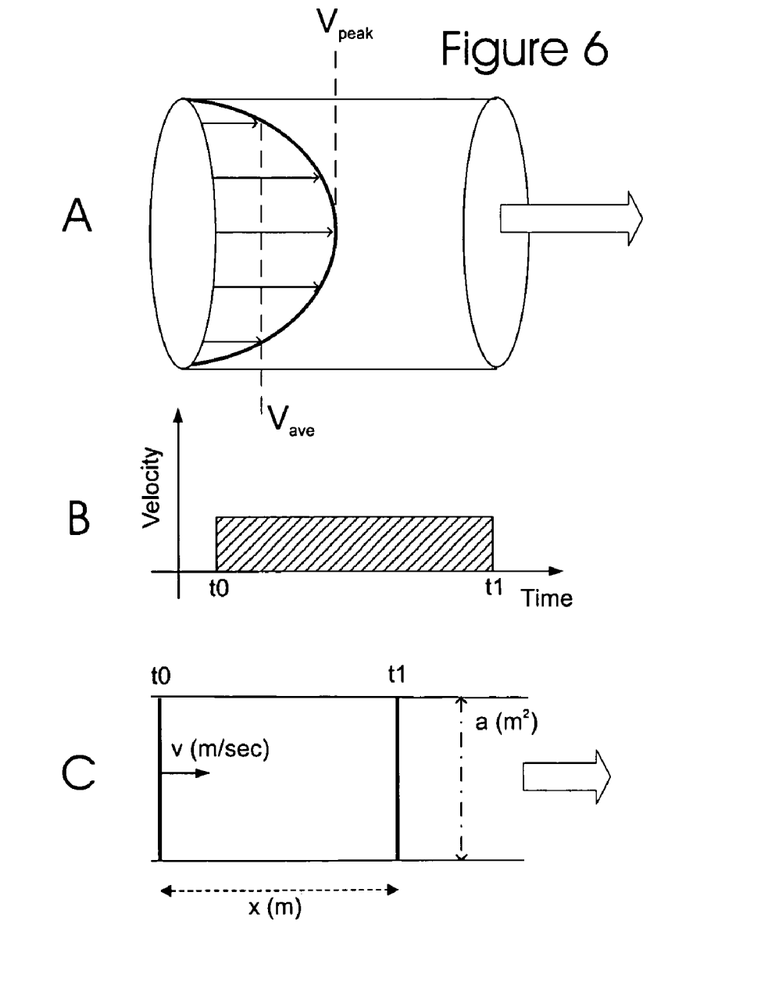
FIG. 6 illustrates the basis of Doppler measurement used in the present invention by delineating streamlined flow through a vessel, its profile through time and the basis of the time-integral area product showing volume of flow.
Figures 7, 8:
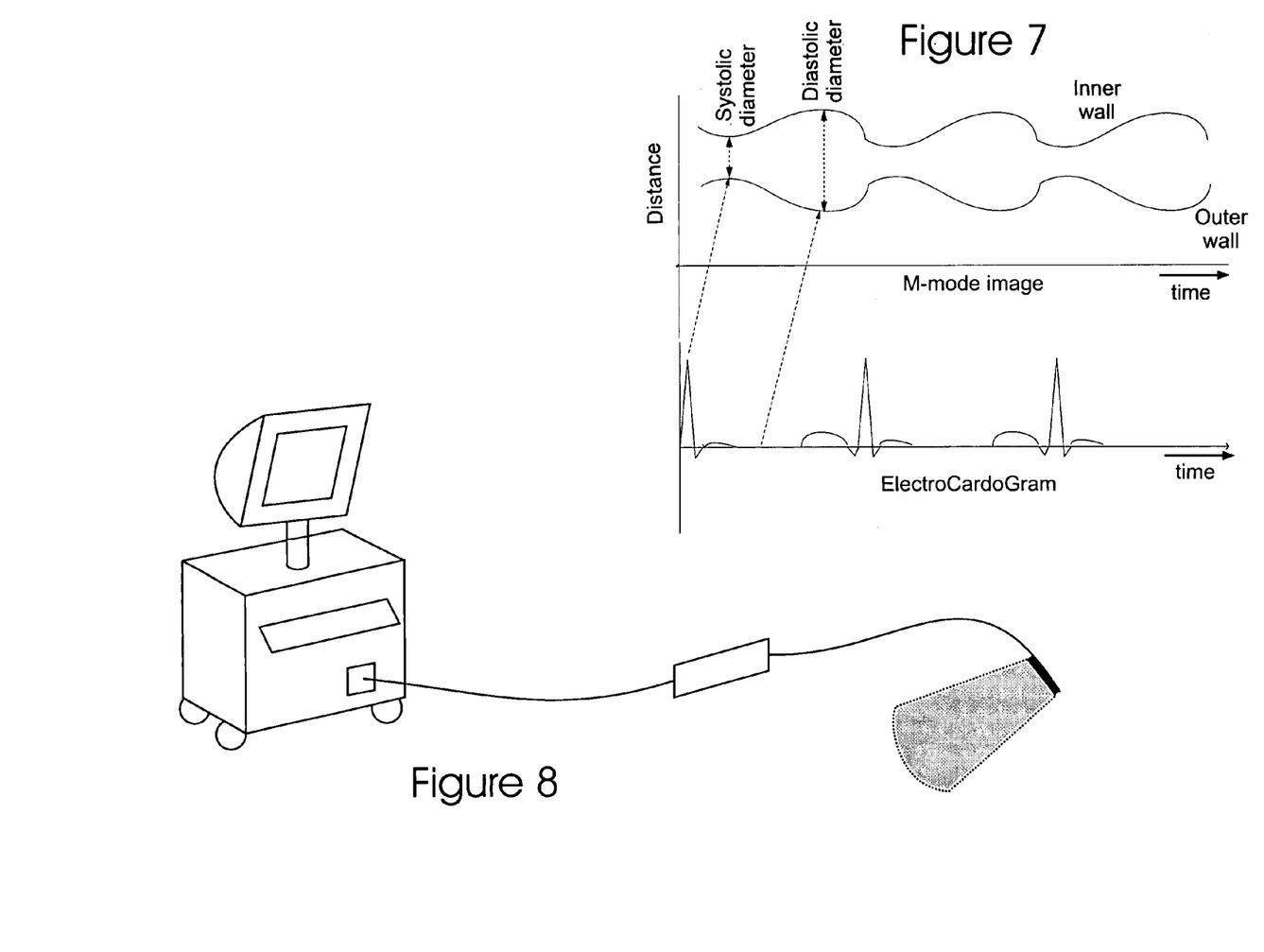
FIG. 7 illustrates the basis of M-mode measurement used in the present invention. Two walls of the ventricle are viewed using M-mode. Once cross section is shown relative to the associated electrocardiogram.
FIG. 8 provides a perspective view of an ultrasound system for use in the present invention including the ultrasound console, connecting isolation box, and the ultrasound catheter. The isolation box provides electrical isolation between the patient and the ultrasound system as required by current FDA guidelines.

Such a catheter could be placed in either the right atrium of the heart or the right ventricle and easily allow viewing of the left ventricle (FIG. 7). Another approach for viewing could be from the outside of the heart, via an incision through the chest of a patient. This catheter would connect either directly to a display system or through a connecting cable, as shown in FIG. 6. The ultrasound display can provide a display of the measurement of cardiac output in assisting the physician with the procedure.

In addition to ultrasound imaging, a number of other items may make this implant an easier procedure, especially since many of the heart failure physicians may not have previously implanted pacemakers, may not have access to x-ray fluoroscopy, may have limited budgets for capital equipment, and may desire all discreet components used in an implantation to be accessible through one keyboard, allowing for better patient data management. Some of these improvements include:

1. Combining the ultrasound with a robust cardiac electrophysiology recording device such that both surface electrocardiograms and internal electrocardiograms can be recorded and displayed. Both electrograms, while not necessary, could substantially assist in the procedure.

2. Currently all pacemakers programmers are provided in discreet hardware. Combining this with a comprehensive electrophysiology recording device could eliminate errors of input, reduce duplication of demographic data, and allow all data to be recorded in one database at one time.

3. The left ventricle electrode can be implanted in a spot chosen by imaging as well as voltage mapping. An overlay of these two parameters could more easily allow the physician to visualize the mechanical and electrical characteristics at the same time.

4. Often times the heart failure patient has a number of co-morbidities showing symptoms at the same time, such as atrial fibrillation, ventricular tachycardias, and renal failures, among others. Atrial fibrillation and ventricular tachycardia can be brought under control via electrical shock cardioversion, either internally with catheters, or externally, although with much higher energy, with patches or paddles. A cardioversion device which could utilize the same electrodes that are otherwise introduced into the heart for pacemaker implantation, would be advantageous if also integrated with the overall electrophysiology system. In this manner, inadvertent shocks could be avoided as the trigger mechanism would come from the ventricular signal from the internal electrode. Thus, in one embodiment, the ultrasound imaging system of the present invention also comprises an integral defibrillation system whereby, if needed, internal cardiac defibrillation can be implemented quickly and easily. The integrated defibrillation electrode or system may be incorporated into the ultrasound imaging catheter, attached to the ultrasound imaging catheter, or as a separate electrode system or catheter which is inserted along with the ultrasound imaging catheter.

BRIEF DESCRIPTION OF THE DRAWINGS

FIG. 9 generally illustrates an normal heart (i.e., non-congestive failure (CHF) heart). Panel A illustrates the right atrium (RA), left atrium (LA), right ventricle (RV), and left ventricle (LV) as well as the location of an electrode ("lead") placed on the right ventricle to provide electrical pulses to the heart; the directions of the normal pacing pathways are also shown. Panel B illustrates the direction of normal contraction of the heart muscle in the ventricles.

FIG. 10 generally illustrates a CHF heart with enlargement of the left ventricle. Panel A illustrates the enlargement of the left ventricle normally observed with CHF; the dotted line in the left ventricle is included to illustrate the normal heart (i.e., non-CHF) as shown in FIG. 9. Panel B generally illustrates the area slow conduction and the normal area for placement of an electrode for re-synchronization. Panel C generally illustrates the direction of potential contraction normally associated with CHF without re-synchronization.

FIG. 11 generally illustrates placement of the ultrasound catheter of this invention in the right ventricle to image the left ventricle according to one embodiment of the present invention.

FIG. 12 provides computer flowcharts illustrating the procedures for estimating cardiac output using Doppler based techniques (Panel A) and M-mode based techniques (Panel B).

DETAILED DESCRIPTION OF THE PREFERRED EMBODIMENT

The present invention provides an ultrasound imaging system suitable for measuring cardiac output of a patient's heart, said system comprising:

(1) an ultrasound imaging catheter comprising at least one transducer utilizing piezoelectric properties to generate acoustic signals from electrical signals in order to obtain ultrasound signals, wherein the at least one transducer is suitable for insertion into the patient's heart and to obtain ultrasound signals associated with an area of the patent's heart in which cardiac output is to be measured;

(2) digital and/or analog electronics capable of generating and processing ultrasound signals from the at least one transducer to generate B-mode, M-mode, or Doppler representations of the cardiac output of the patient's heart; and (3) an associated computer that can generate and process the ultrasound signals in order to measure the cardiac output in the patient's heart.

This invention also provides a method of placing an electrode at a desired position at or near the left ventricle of a patient's heart in order to electrically activate the left ventricle of the patient's heart using the electrode, said method comprising:

(1) advancing the electrode to the proximity of the upper left ventricle;

(2) placing an ultrasound imaging catheter in a position to image the left ventricle of the patient's heart, wherein the ultrasound imaging catheter comprises at least one transducer utilizing piezoelectric properties to generate acoustic signals from electrical signals in order to obtain ultrasound signals and wherein the at least one transducer is suitable for insertion into the patient's heart and to obtain ultrasound signals associated with an area of the patent's heart;

(3) utilizing the ultrasound imaging catheter to image the electrode at or near the left ventricle of a patient's heart and to guide the electrode to the desired position; and (4) attaching the electrode to the desired position. One preferred desired position for attachment of the electrode is the upper portion of the left ventricle (i.e., nearer the base of the heart as compared to the apex). In one preferred embodiment, at least one transducer has a defecting or rotation element whereby the transducer, once positioned to image the left ventricle of the patient's heart, can be easily rotated or moved in order to image other portions of the patient's heart.

The present invention also provides an ultrasound imaging system to assist in cardiac electrophysiology procedures related to a patient's heart, said system comprising:

(1) an ultrasound imaging catheter comprising a multi-element array transducer utilizing piezoelectric properties to generate acoustic signals from electrical signals in order to obtain ultrasound signals, wherein the multi-element array transducer is suitable for insertion into the patient's heart and to obtain ultrasound signals associated with the patent's heart;

(2) digital and/or analog electronics capable of generating and processing ultrasound signals from the multi-element array transducer to generate and display a representation of (a) the electrocardiogram of the patient's heart, (b) a real time image of the patient's heart, or (c) the cardiac output of the patient's heart. In a preferred embodiment, the representation ultrasound signals can be displayed relative to, and compared to, a voltage conduction map of the patient's heart (i.e., a representation of the progression of electrical activation/deactivation or "action potentials" of the muscles of the heart).

Figure 4:
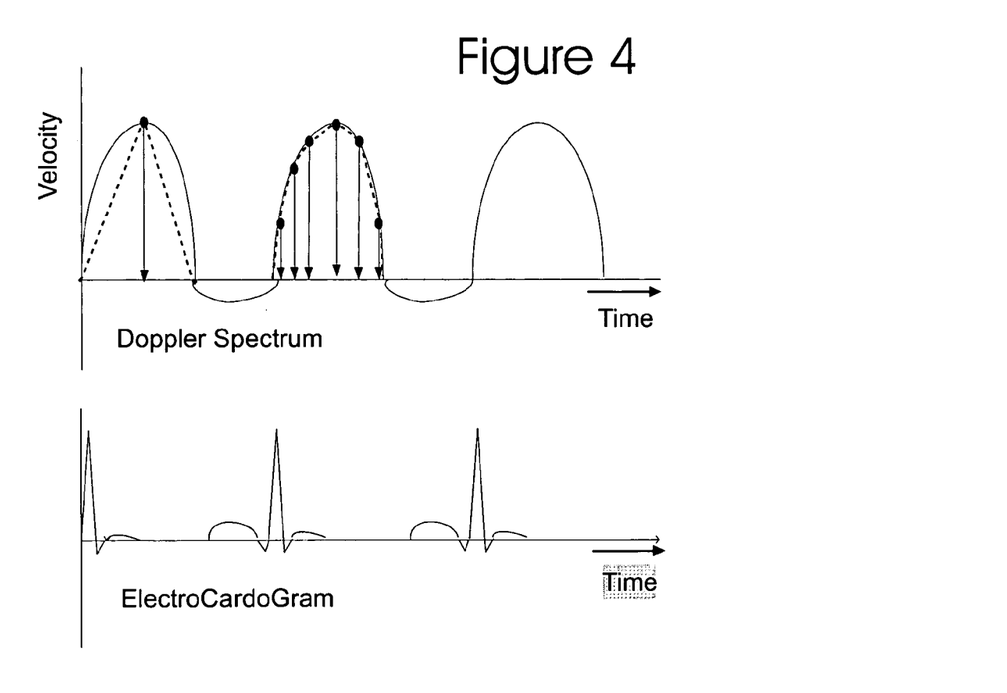
FIG. 4 provides a genera diagram illustrating the basic technique to measure volume of flow from a spectral Doppler spectrum, and the approximate correlation of the ECG with the Doppler spectrum readout. The flow being samples is at the aortic valve (as shown in FIG. 3). Multiple peak velocity points can be utilized as shown in the first and second Doppler waveforms with increasing number of points providing increase accuracy.

The basis of the measurement/estimation process of the present invention is shown in FIGS. 6 and 7. Using the Doppler process (FIG. 6), the amplitude of the velocity profile is halved to provide the average velocity across the flow area (FIG. 6A). The velocity is integrated (FIG. 6B) with respect to time from the start of the pulse (t0) to the end of the pulse (t1). Such integration can also include the negative peaks shown in FIG. 4A to compensate for reverse flows. The result of this integration with respect to time is then multiplied by the cross-sectional area of the flow to provide the ejection volume (FIG. 6C). The integration length can also be set by integrating during the complete cardiac cycle (i.e., through one complete cycle of the ECG). The spectrum in FIG. 6 can also be obtained by either frequency and/or amplitude plotting of an audio signal.

$$V_{ejt} = A \int \frac{V_{peak}}{2} dt \qquad \text{Eq. 1}$$

where $V_{ejt}$=Ejection volume/stroke volume;

A=cross sectional area of flow; and $V_{peak}$=points on the velocity curve.

Using the M-mode process (FIG. 7), the system outputs the relative position of the two walls of the ventricle as a function of time. The ventricle can be equated to an ellipsoid shape, whose secondary radius is represented by the distance between the two walls measured by the M-mode. The primary equation to the volume would then be $$V = (\pi(R_1 + C_1)R_2)(2\pi R_2) \pm C_2 \qquad \text{Eq. 2}$$

where V=volume $R_1$=Primary radius=length of the ventricle;

$R_2$=secondary radius=distance between the walls of the ventricle;

$C_1$=a correction factor to compensate for the difference in morphology of the ventricle w.r.t. an ellipse; and $C_2$=correction in the primary radius to compensate for longitudinal contractility of the ventricle during a cardiac cycle.

Volume can then be calculated at systole and diastole (determined either with correlation to the ECG, as shown in FIG. 7 or by determining the minimum and maximum of the M-mode curve). The stroke volume is then given by $$V_{SV} = V_{diastole} - V_{systole} \qquad \text{Eq. 3}$$

Figure 1:
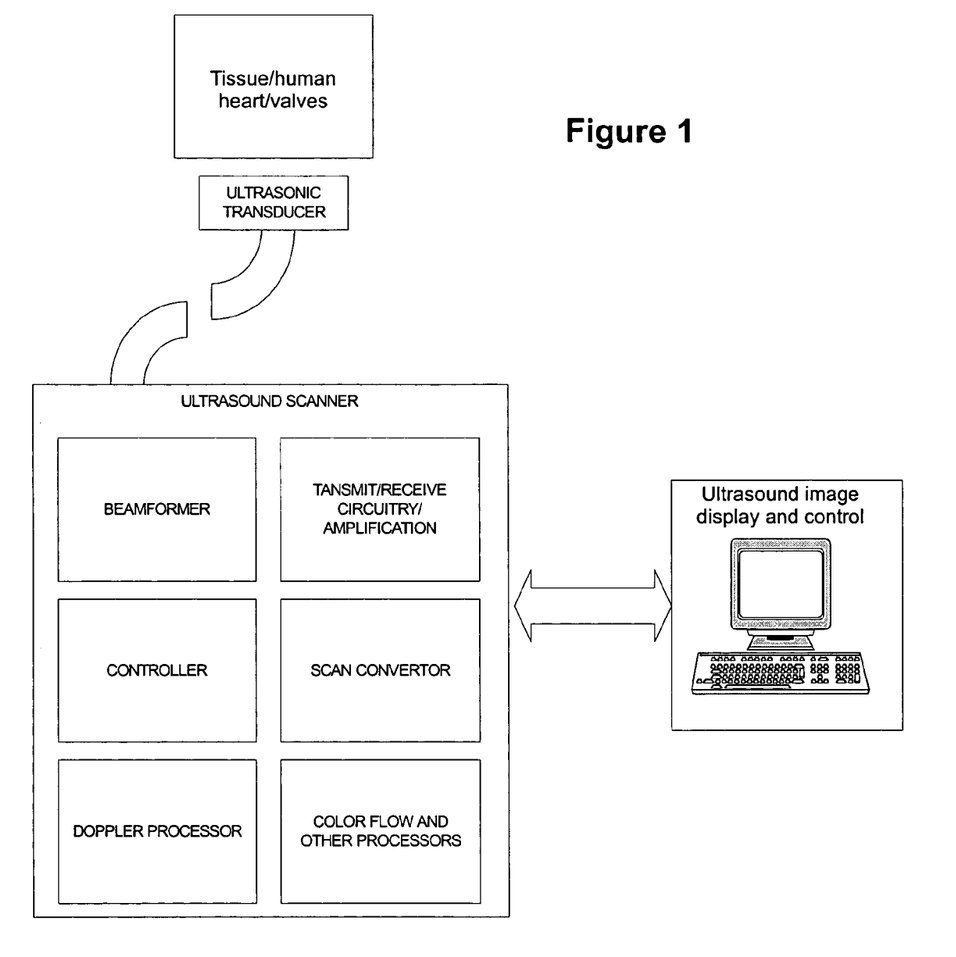
FIG. 1 provides a general system diagram showing an ultrasound system.
Figure 5:
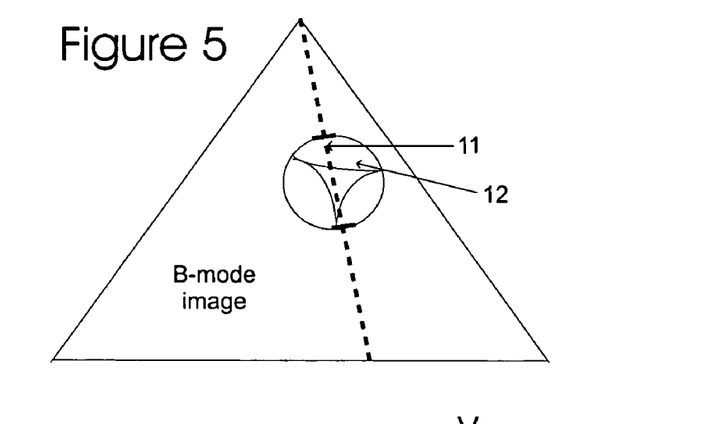
FIG. 5 provides a diagram illustrating the measurement technique for calculating cross-sectional area of the output from the ventricle. In this view, the ultrasound catheter is positioned in the vena-cavae or in the right atrium. Other anatomical locations for placement of the ultrasound catheter can, of course, be used.

One embodiment of the present invention is in the form of hardware and/or software that exists as part of the ultrasound scanner (FIG. 1). In such an embodiment, the system utilizes the Doppler processing capabilities of the host ultrasound scanner to obtain a time-varying signal representative of the velocity of flow through an area of interest. Such area could include the inlet of the aorta from the left ventricle, or the valve in between. The system also utilizes a view/measure of the cross-sectional area through which the flow of interest is to pass (FIG. 5).

Figure 3:
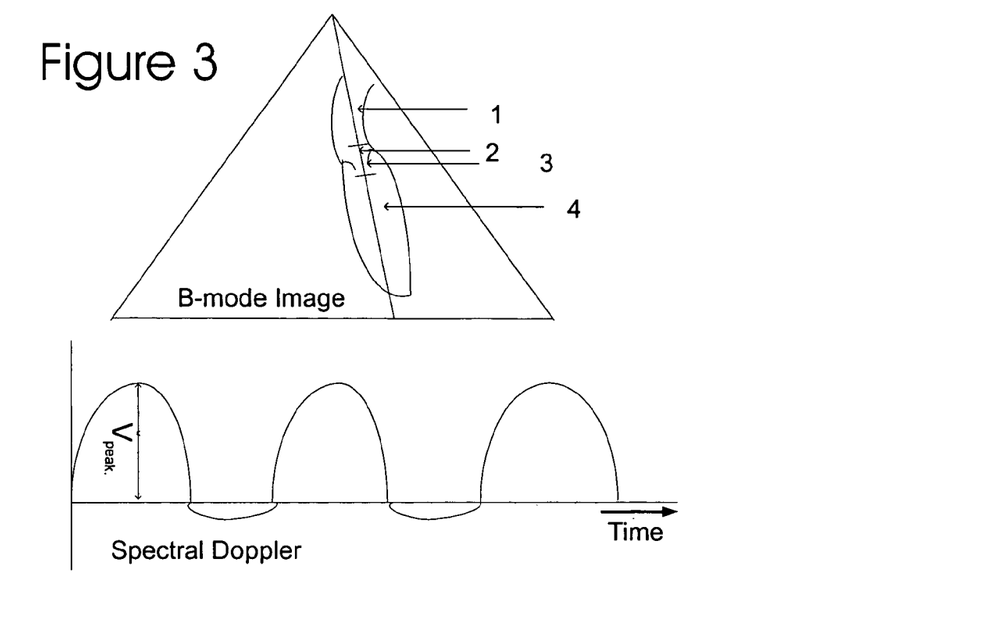
FIG. 3 provides diagrams of a typical B-mode image and an associated Doppler spectrum. A cross-sectional view of the ventricle and the aortic value are shown as viewed from the right atrium. The spectral Doppler waveform shows the velocity profile of the flow at the aortic valve.

The Doppler system outputs the spectral information, which is indicative of the velocity of flow through the volume of interest (as shown in FIG. 3) either by means of showing a spectrum (which in some embodiments can be obtained in a analog or digital format from the machine). Such a spectrum can be obtained either by obtaining a longitudinal sectional view of the flow axis at any angle (as represented in FIG. 3), or by obtaining a cross sectional view of the flow conduit (FIG. 5). Such calculations of flow/area can be compensated for the angle of measurement using a cosine of the angle w.r.t. actual plane correction. For conditions where the flow is perpendicular to the sample volume of the Doppler system, other estimation techniques such as "Transverse Doppler," which utilizes the Doppler bandwidth to assess flow at flow to beam angles close to 90 degrees, can be utilized. Tortoli et al., *Ultrasound Med. Biol.,* 21, 527–532 (1995). This Doppler signal can also be as an audio signal (again, either in analog or digital format) as a frequency and/or amplitude modulated signal that is indicative of the spectrum and hence the flow velocity through the area of interest. This could further include ECG signals (again, in analog or digital format).

Further processing can be carried out, for example, using the following techniques:

1. A largely manual process wherein the user measures/demarcates, either with or without the aid of an ECG, the peak velocities at least one point on the spectrum and demarcates/measures the cross-section of the outlet of the ventricle; and the system/calculating tool (either on the ultrasound machine or on a separate computer) the integrates the curve over time to obtain stroke volume via Equation 1.

2. A semi-automated process wherein the system (either on the ultrasound machine or separate) automatically integrates the curve with or without the help of an ECG while the user inputs the area of interest of the orifice through which the flow passes.

3. A fully automated process wherein the system prompts the user to obtain particular views of the anatomy of interest and demarcate specific points and the system then processes the data as above with, however, the system internally tracking the data of interest.

4. The system automatically integrates the curve from beat to beat, and outputs the stroke volume in any sort of display, having obtained the cross sectional area using the techniques mentioned in point 2 or 3 above. Of course, various combinations and/or modifications of these techniques can be used if desired and depending on the particular application and/or patient.

Another embodiment of the present invention is in the form of hardware and/or software that exists separate from the ultrasound scanner console or workstation with means to communicate either video and/or audio and/or other signals between the ultrasound scanner and/or the display computer/system. Communication between such workstation and the ultrasound scanner could include video, audio, and/or any ECG signals in digital and/or analog format. The above described processing can then be performed either partially or entirely on the workstation.

Figure 2A:
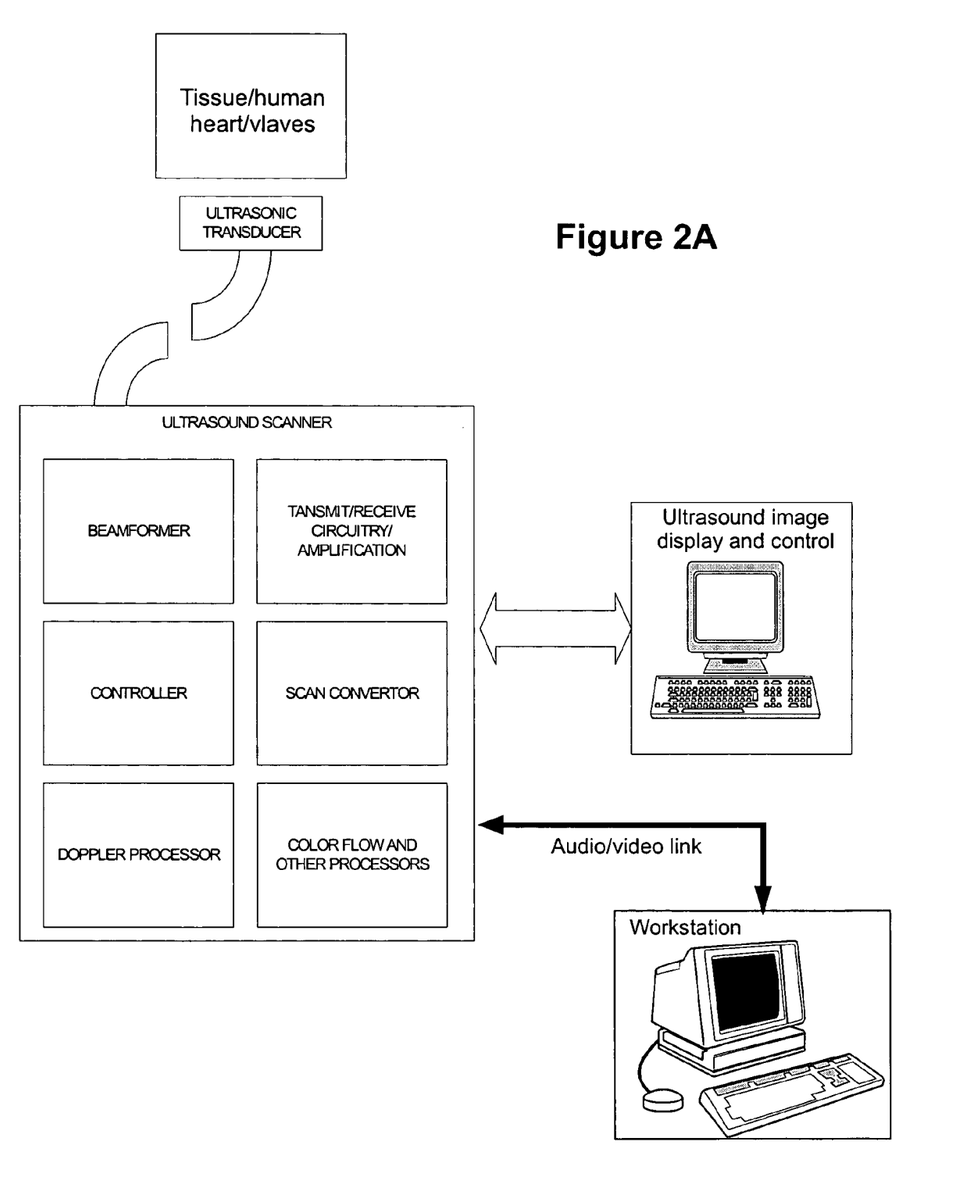
FIGS. 2A, 2B, and 2C provides various embodiments of the present system with an attached workstation.
Figure 2B:
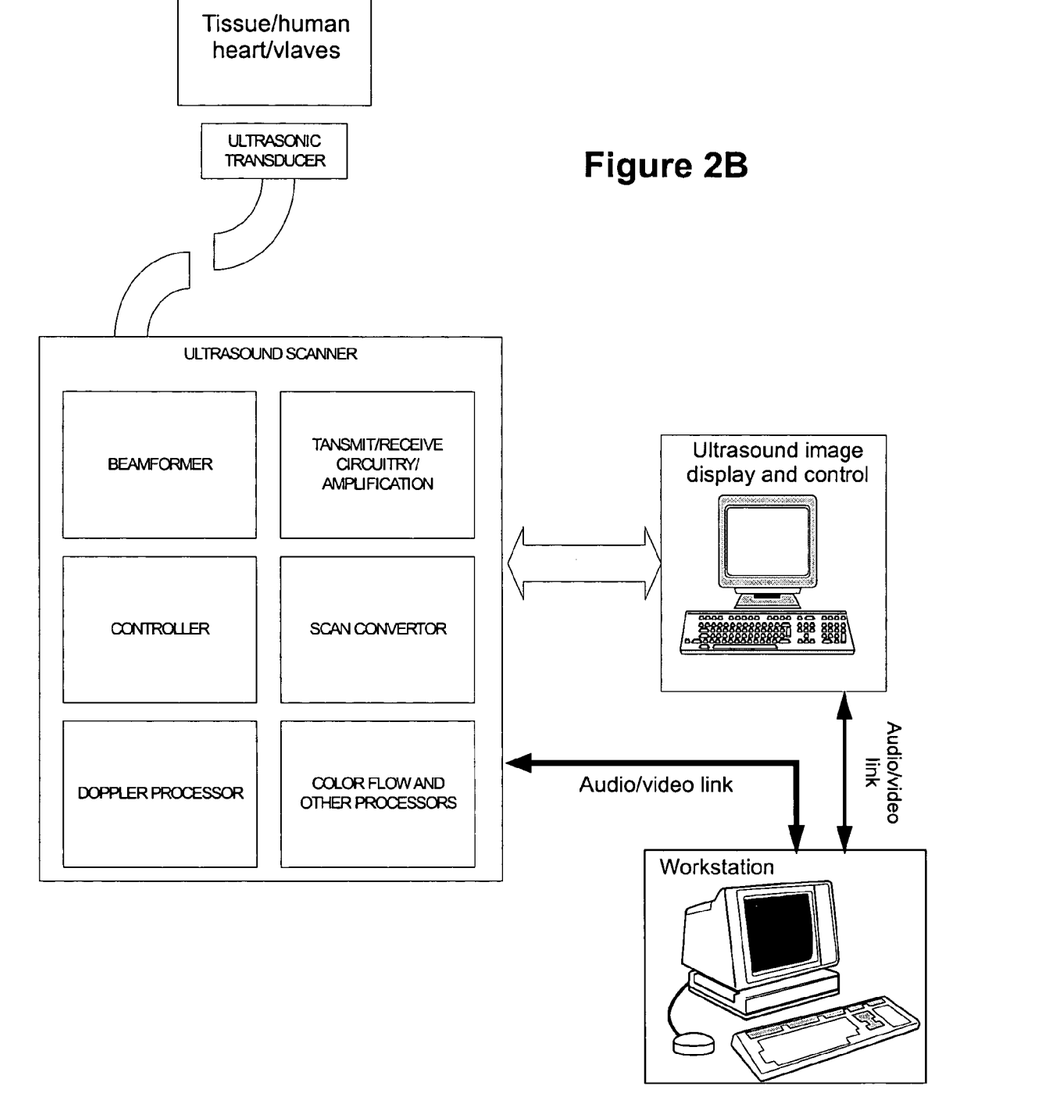
Figure 2C:
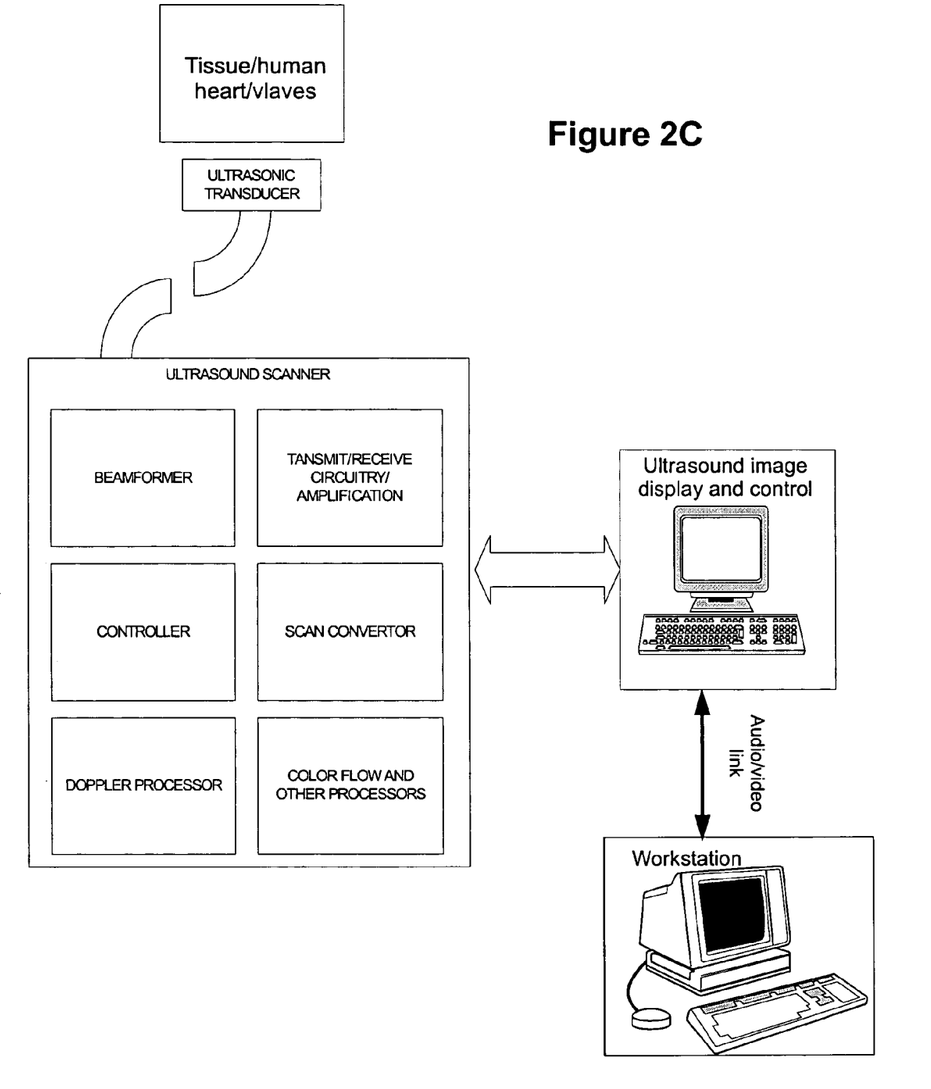

In another embodiment of the present invention, the M-mode output is utilized to measure stroke volume. Again, this system can comprise of hardware and/or software that resides wholly on the ultrasound scanner or can also include hardware and/or software on a separate workstation with means to communicate either digital and/or analog data with the ultrasound scanner (FIGS. 1 and 2). The volume can then be estimated, as given earlier by Equations 2 and 3 (FIG. 7).

Processing can be carried out, for example, using the following techniques:

1. A largely manual process wherein the user measures/demarcates, either with or without the aid of an ECG, the systolic and diastolic distances between the two ventricular walls, and the system/calculating tool (either on the ultrasound machine or on a separate computer) calculates the stroke volume. This process can include, if desired, provisions for the user or system to record/obtain the correction factors described in Equation 2.

2. A semi-automated process wherein the system (either on the ultrasound machine or separate) automatically measures the distances and estimates the stroke volume with or without the help of an ECG. In this case, the system can automatically measure/estimate the correction factors described in Equation 2, or the user can specify or aid the system in estimating/measuring these factors.

3. A fully automated process wherein the system prompts the user to obtain particular views of the anatomy of interest and demarcate specific points and the system then processes the data as above with, however, the system internally tracking the data of interest.

4. The system automatically measures the stroke volume, with data obtained from any of the above described methods, and outputs the stroke volume in any sort of display, having obtained the cross sectional area using the techniques mentioned in points 2 or 3 above.

A yet another embodiment can include hardware and/or software separate from the ultrasound scanner, in the form of a workstation wherein there exists a mode of communication, either analog or digital, between the workstation and the ultrasound scanner or catheter. Cabling from the ultrasound machine to the catheter (especially with a multi element array catheter) and from the catheter proximal connector to the catheter transducer housed at the distal tip can be expensive. To reduce cost, the ultrasound machine could be moved adjacent to the patient, thereby allowing a relatively short cable to be used to attach the catheter. In some cases, however, this may be impractical since most catheter rooms are sterile or semi-sterile environments and, thus, the ultrasound machine may be some distance from the patient's bedside. Thus, a connecting cable which is reusable (and probable non-sterile) is desirable, as opposed to the catheter itself, which is sterile and usually not re-usable. It would be desirable if this connecting cable could be used as a universal cable in that it could be used with many ultrasound machines. While many ultrasound machines have a standard 200 pin ZIP connector, most ultrasound machines do not have patient isolation means built in to the degree necessary for percutaneous catheter use. Therefore, in another embodiment, the system of this invention employs a connector cable with an isolation means or isolation box that is external to the ultrasound machine itself. Preferably the isolation box, which houses a plurality of isolation transformers, is relatively small so that it could be placed easily on or near the patient's bed. Such a cable could easily accommodate all operational communication between the catheter and the ultrasound machine and/or the appropriate computer workstation.

In still another embodiment, the ultrasonic catheter further comprises a temperature sensing and/or control system. Especially when used at higher power (e.g., when using color Doppler imaging) and/or for lengthy periods of time, it is possible that the transducer, and hence, the catheter tip, generate heat that may damage tissue. While computer software can be used to regulate the amount of power put into the catheter to keep the temperature within acceptable ranges, it is also desirable to provide a temperature sensing means as well as a safety warning and/or cut-off mechanism for an additional margin of safety. Actual temperature monitoring of the catheter tip is most desirable, with feedback to the computer, with an automatic warning or shut down based upon some predetermined upper temperature limit. The system could be programed to provide a warning as the temperature increases (e.g., reaches 40° C. or higher) and then shut off power at some upper limit (e.g., 43° C. as set out in U.S. FDA safety guidelines). To monitor the temperature at or near the tip of the catheter (i.e., in the region of the ultrasound transducer), a thermistor may be used. The temperature at the tip of the catheter could be continuously monitored via appropriate software. Although the software could also provide the means to control the power to the catheter in the event that excessive temperatures are generated, it would also be desirable to have a back up shut off or trip mechanism (e.g., a mechanical shut off or tripping means).

Of course, various combinations and/or modifications of these techniques and systems can be used if desired and depending on the particular application and/or patient.

It is to be understood, however, that even though numerous characteristics and advantages of the present invention have been set forth in the foregoing description, along with details of the structure and function of the invention, the disclosure is only for illustrative purposes. Changes may be made in detail, especially in matters of shape, size, arrangement, and storage/communication formats within the principles of the invention to the full extent indicated by the broad general meaning of the terms in which the appended claims are expressed.

What is claimed is:

1. An ultrasound imaging system suitable for use in measuring cardiac output of a patient's heart and simultaneously imagine the left ventricle area of the heart for accurate placement of a pacing electrode, said system comprising:

(1) an ultrasound imaging catheter designed for intracardiac use comprising at least one transducer utilizing piezoelectric properties to generate acoustic signals from electrical signals in order to obtain ultrasound signals, wherein the at least one transducer is suitable for insertion into the patient's heart and to obtain ultrasound signals associated with an area of the patent's heart in which cardiac output is to be measured;

(2) digital and/or analog electronics capable of generating and processing ultrasound signals from the at least one transducer to generate B-mode, M-mode, or Doppler representations of the cardiac output of the patient's heart; and (3) an associated computer that can generate and process the ultrasound signals in order to simultaneously measure the cardiac output in the patient's heart and display an image of the area of the patient's heart.

2. The ultrasound imaging system of claim 1, wherein the system can additionally provide a representation of the ECG of the patient's heart.

3. The ultrasound imaging system of claim 1, wherein the ultrasound signals are used to generate the M-mode representation of the cardiac output.

4. The ultrasound imaging system of claim 1, wherein the ultrasound signals are used to generate the Doppler representation of the cardiac output.

5. The ultrasound imaging system of claim 1, wherein the at least one transducer has a tube size of 12 French or less.

6. The ultrasound imaging system of claim 2, wherein the at least one transducer is a phased array transducer having a plurality of ultrasonic energy generation units.

7. The ultrasound imaging system of claim 3, wherein the at least one transducer is a phased array transducer having a plurality of ultrasonic energy generation units.

8. The ultrasound imaging system of claim 4, wherein the at least one transducer is a phased array transducer having a plurality of ultrasonic energy generation units.

9. The ultrasound imaging system of claim 1 further comprising defibrillation electrodes whereby, if and when needed, internal cardiac defibrillation can be carried out.

10. The ultrasound imaging system of claim 1 further comprising a temperature sensing device adjacent to the at least one transducer to monitor temperature near the at least one transducer and a mechanism provide a warning or to shut off power to the at least one transducer if the temperature near the at least one transducer rises above a predetermined level.

11. A method of placing an electrode at a desired position at or near the left ventricle of a patient's heart in order to electrically activate the left ventricle of the patient's heart using the electrode and simultaneously measuring the cardiac output of the patient's heart, said method comprising:
  (1) advancing the electrode to the proximity of the upper left ventricle;
  (2) placing an ultrasound imaging catheter in a position to image the left ventricle of the patient's heart, wherein the ultrasound imaging catheter comprises at least one transducer utilizing piezoelectric properties to generate acoustic signals from electrical signals in order to obtain ultrasound signals and wherein the at least one transducer is suitable for insertion into the patient's heart and to obtain ultrasound signals associated with an area of the patent's heart and the cardiac output of the heart;
  (3) utilizing the ultrasound imaging catheter to simultaneously measure the cardiac output of the heart and image the electrode at or near the left ventricle of a patient's heart and to guide the electrode to the desired position; and
  (4) attaching the electrode to the desired position.

12. The method of claim 11, wherein the desired position is an upper portion of the left ventricle.

13. The method of claim 11, wherein the ultrasound signals are used to generate a Doppler representation of cardiac output of the patent's heart and the Doppler representation is used to assist in determining the desired position.

14. The method of claim 13, wherein the Doppler representation of cardiac output is generated for different locations of the electrode or from different pacing parameters of the electrode and the cardiac output from the different location or different pacing parameters are compared in order to determine the desired position or desired pacing parameters.

15. The method of claim 12, wherein the electrode is advanced endocardially or epicardially.

16. The method of claim 11, where the at least one transducer comprises a linear array type transducer, a curved linear array type transducer, or a phased array type transducer.

17. The method of claim 11, wherein the at least one transducer has a tube size of 12 French or less.

18. The method of claim 11, wherein the at least one transducer is a phased array transducer having a plurality of ultrasonic energy generation units.

19. The method of claim 11, wherein the at least one transducer is a phased array transducer having a plurality of ultrasonic energy generation units.

20. The method of claim 13, wherein the cardiac output is determined as stroke volume, ejection fraction, or flow rate.

21. The method of claim 11, wherein the at least one transducer, once positioned to image the left ventricle of the patient's heart, can be rotated to image other portions of the patient's heart.

22. The method of claim 11, wherein the ultrasound imaging catheter further comprises defibrillation electrodes whereby, if and when needed, internal cardiac defibrillation can be carried out during the method.

23. The method of claim 13, wherein the ultrasound imaging catheter further comprises defibrillation electrodes whereby, if and when needed, internal cardiac defibrillation can be carried out during the method.

24. The method of claim 13, wherein the ultrasound imaging catheter further comprises a temperature sensing device adjacent to the at least one transducer to monitor temperature near the at least one transducer and a mechanism provide a warning or to shut off power to the at least one transducer if the temperature near the at least one transducer rises above a predetermined level.

25. An ultrasound imaging system suitable for use in measuring cardiac output of a patient's heart and simultaneously imaging the left ventricle area of the heart for accurate placement of a pacing electrode, said system comprising:
  (1) an ultrasound imaging catheter designed for intracardiac use comprising a multi-element array transducer utilizing piezoelectric properties to generate acoustic signals from electrical signals in order to obtain ultrasound signals, wherein the multi-element array transducer is suitable for insertion into the patient's heart and to obtain ultrasound signals associated with the patent's heart;
  (2) digital and/or analog electronics capable of generating and processing ultrasound signals from the multi-element array transducer to generate and display a representation of the electrocardiogram of the patient's heart a real time image of the patient's heart.

26. The ultrasound imaging system of claim 25, wherein electrocardiogram of the patient's heart is a surface or an intracardiac electrocardiogram.

27. The ultrasound imaging system of claim 25, wherein the multi-element array transducer has a tube size of 12 French or less.

28. The ultrasound imaging system of claim 25, wherein the multi-element array transducer is a phased array transducer having a plurality of ultrasonic energy generation units.

29. The ultrasound imaging system of claim 27, wherein the multi-element array transducer is a phased array transducer having a plurality of ultrasonic energy generation units.

30. The ultrasound imaging system of claim 25, wherein the cardiac output is determined as stroke volume, ejection fraction, or flow rate.

31. The ultrasound imaging system of claim 25, where the representation ultrasound signals can be displayed relative to, and compared to, a voltage conduction map of the patient's heart.

32. The ultrasound imaging system of claim 25 further comprising an integrated pacemaker programmer such that operating parameters of a pacemaker attached to, or in electrical communication to, the patient's heart can be monitored and modified in order to determine optimal or near-optimal operating parameters based on information from the ultrasound signals from the multi-element array transducer.

33. The ultrasound imaging system of claim 25 further comprising defibrillation electrodes whereby, if and when needed, internal cardiac defibrillation can be carried out.

34. The ultrasound imaging system of claim 33, wherein the defibrillation electrodes are incorporated into the ultrasound imaging catheter.

35. The ultrasound imaging system of claim 25, wherein the ultrasound imaging catheter further comprises a temperature sensing device adjacent to the at least one transducer to monitor temperature near the at least one transducer and a mechanism provide a warning or to shut off power to the at least one transducer if the temperature near the at least one transducer rises above a predetermined level.

* * * * *

UNITED STATES PATENT AND TRADEMARK OFFICE
CERTIFICATE OF CORRECTION

| | | |
|---|---|---|
| PATENT NO. | : 7,211,045 B2 | Page 1 of 1 |
| APPLICATION NO. | : 10/620517 | |
| DATED | : May 1, 2007 | |
| INVENTOR(S) | : Praveen Dala-Krishna et al. | |

It is certified that error appears in the above-identified patent and that said Letters Patent is hereby corrected as shown below:

Claim 1, Column 10, Line 38; change "imagine" to --imaging--; and

Signed and Sealed this

Thirty-first Day of July, 2007

JON W. DUDAS
*Director of the United States Patent and Trademark Office*